US012157877B2

(12) United States Patent
Coffman et al.

(10) Patent No.: US 12,157,877 B2
(45) Date of Patent: Dec. 3, 2024

(54) CELL RETENTION DEVICE AND METHOD

(71) Applicant: Boehringer Ingelheim International GmbH, Ingelheim am Rhein (DE)

(72) Inventors: Jonathan Coffman, Union City, CA (US); Scott Godfrey, Pleasanton, CA (US); Samantha Wang, San Francisco, CA (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/092,482

(22) PCT Filed: Apr. 13, 2017

(86) PCT No.: PCT/US2017/027318
§ 371 (c)(1),
(2) Date: Oct. 10, 2018

(87) PCT Pub. No.: WO2017/180814
PCT Pub. Date: Oct. 19, 2017

(65) Prior Publication Data
US 2019/0169559 A1    Jun. 6, 2019

Related U.S. Application Data

(60) Provisional application No. 62/330,912, filed on May 3, 2016, provisional application No. 62/322,825, filed on Apr. 15, 2016.

(51) Int. Cl.
*C12M 3/00* (2006.01)
*B01L 3/00* (2006.01)
*C12M 1/00* (2006.01)

(52) U.S. Cl.
CPC ............ *C12M 29/10* (2013.01); *C12M 29/16* (2013.01); *C12M 47/02* (2013.01)

(58) Field of Classification Search
CPC ...... C12M 25/02; C12M 29/04; C12M 47/02; C12M 33/14
See application file for complete search history.

(56) References Cited

U.S. PATENT DOCUMENTS 5,166,067 A * 11/1992 Ishida .................... C12M 29/02
  435/296.1
6,544,424 B1    4/2003 Shevitz
(Continued)

FOREIGN PATENT DOCUMENTS

| WO | 2000046354 A1 | 8/2000 |
| WO | 2008109674 A2 | 9/2008 |
| WO | 2010003759 A2 | 1/2010 |

OTHER PUBLICATIONS

Bonham-Carter, John et al "A Brief History of Perfusion Biomanufacturing" (2011) BioProcess International, 9 (9), 5 pgs.
(Continued)

*Primary Examiner* — Nathan A Bowers
(74) *Attorney, Agent, or Firm* — Mary Breen Smith

(57) ABSTRACT

The subject technology relates to a cell retention device and method for use in a perfusion cell culture system where the cell retention device includes a hollow-fiber filter having an average pore size ranging from about 0.5 to about 20 µm and having the ability to operate under perfusion cell culture conditions for up to 35 days without being clogged or losing its product sieving ability by more than 20%.

3 Claims, 12 Drawing Sheets

(56) References Cited

U.S. PATENT DOCUMENTS

| | | | |
|---|---|---|---|
| 2008/0131934 A1 | 6/2008 | Crowley et al. | |
| 2009/0042253 A1* | 2/2009 | Hiller | C12P 21/00 |
| | | | 435/70.3 |
| 2011/0086411 A1 | 4/2011 | Grillberger et al. | |
| 2011/0201050 A1 | 8/2011 | Niazi | |
| 2013/0059371 A1 | 3/2013 | Shevitz | |
| 2015/0158907 A1* | 6/2015 | Zhou | C12M 29/00 |
| | | | 530/399 |
| 2016/0312168 A1* | 10/2016 | Pizzi | C12M 47/02 |
| 2017/0292103 A1* | 10/2017 | Cattaneo | C12M 29/04 |
| 2018/0361325 A1* | 12/2018 | Hiraoka | C12M 25/10 |
| 2019/0169559 A1 | 6/2019 | Coffman et al. | |

OTHER PUBLICATIONS

International Search Report PCT/US2017/027318, mailed Jul. 18, 2017.

Woodside, Steven M. et al. "Mammalian cell retention devices for stirred perfusion bioreactors" (1998) Cytotechnology, 28, 163-175.

Wang et al., "Larger Pore Size Hollow Fiber Membranes as a Solution to the Product Retention Issue in Filtration-Based Perfusion Bioreactors", Biotechnology Journal, 2019, pp. 1-6.

* cited by examiner

CELL RETENTION DEVICE AND METHOD

FIELD

The subject technology relates generally to a cell retention device and method for using same in a perfusion cell culture system. In particular, the subject technology relates to an external cell retention device containing a hollow-fiber filter and a method for using same in a perfusion cell culture system.

BACKGROUND

Perfusion is a cell culture mode for the production of recombinant biological products such as antibodies, therapeutic proteins, blood factors (e.g., coagulation proteins), and enzymes. Unlike the batch or fed-batch modes, the perfusion mode involves retaining the viable cells within the bioreactor while continually removing the spent media and products from the bioreactor and replacing them with fresh media. In the presence of fresh media, cells continue to propagate and produce more products. A separation device, i.e., a cell retention device, is therefore required in perfusion to retain the viable cells within the bioreactor while allowing the spent media and products to exit.

Many cell retention devices perform well, to a greater or lesser degree, at small scale, including those based on centrifugal force (centrifuges, hydrocyclones), filtration (spin-filters, tangential flow filters (TFF), alternating tangential flow filters (ATF), dynamic filters), gravitational settling, ultrasonic and dielectrophoretic separation. But only a few types, e.g., ATF with spin filters, cell settlers, and centrifuges may be reliable at larger scales and scalable enough for bioindustrial use, says Bonham-Carter et al., a Brief History of Perfusion Biomaufacturing, Bioprocess International, vol. 9(9):24-30, October 2011.

For cell retention devices that operate base on filtration, to sustain long-term perfusion culture performance, filter design and operation must mitigate fouling (clogging) of the filtration surface by cells, cellular debris and macromolecules. Fouling occurs as these components are concentrated at the filter surface by the filtrate flux (flow through the filter), a process known as concentration polarization. Filter fouling not only limits the filtration rate, but may result in ultrafiltration retention of high molecular weight products within the bioreactor. In general, filtration systems are designed such that the accumulation of cells and cellular material is reduced by flow tangential to the filter surface (in e.g., TTF or ATF) at a fluid shear rate that does not negatively affect the viability of cells. The hydrodynamic lift force acting on cells in the shear field may also play a role in reducing filter clogging by cells, cell debris and macromolecules.

The following references are of note in this area: (1) Woodside et al. Mammalian Cell Retention Devices for Stirred Perfusion Bioreactors, Cytotechnology, 28(1-3):163-175, November 1998; (2) US 2011/0201050 and (3) WO2010/003759.

Woodside et al. discusses mammalian cell retention devices for perfusion bioreactors. Woodside et al. point out that a significant problem for a perfusion reactor design and operation is the reliability of the cell retention device, since variation in the cell culture conditions can result in inconsistent post-translational modifications in protein products. They discuss the merits and limitations of a few different technologies for cell retention and their stability for large-scale perfusion.

With regard to cross-flow filters such as hollow-fiber and flat-plate types which are suitable for mammalian cell perfusion applications, Woodside et al. state that the majority of reported cross-flow filters use microporous membranes with 0.2 to 0.65 µm pores. Such relatively small pores might be expected to clog more readily than larger pore filters. However, a 5 µm pore flat-plate filter membrane required changing every 5 days during perfusion with a filter flux of 1 L m$^{-2}$ h$^{-1}$ while 2 and 10 µm diameter pore membranes were replaced every 5 to 7 days during perfusion with a filter flux of 4 L m$^{-2}$ h$^{-1}$. Thus, there is no clear advantage to these larger pore filters, especially considering the poor cell retention efficiency (<70%) of the 10 µm membrane.

US2011/0201050 describes a gas scrubbed perfusion filter in which fine gas bubbles traveling at fast speed are employed to scrub hollow-fiber filters with pore sizes of 5 microns or less to prevent their fouling by cellular debris and macromolecules. By recommending a gas scrubbing step, US2011/0201050 not only makes the design of a cell culture system more complicated but also provides no data about whether or not such a step could actually resolve the fouling problem. Nor does it provide any data for the effects of the scrubbing step on cell culture conditions and on consistency of product yields.

WO2010/003759 describes a cell culture method which uses a retention device with tangential flow and a hollow-fiber filter in which "the pore size preferably is at least 0.1 µm, more preferably at least 0.2 µm; as an upper limit the pose size is preferably not more than 30 µm, more preferably not more than 20 µm". WO2010/003759 requires that the bioreactor's fluid content come in to contact with a gaseous composition containing oxygen before being circulated through the retention device. It is unclear what the function of the "airflow" is in the method/device of WO2010/003759 or whether it is a scrubbing means as taught in US2011/0201050. In any event, WO2010/003759 does not provide any actual data supporting the theory it proposes and appears to be concerned mainly with the transfer of oxygen to a cell culture. Nor does it an answer to the question of whether or not its method/device works in practice to resolve the fouling or sieving problems in filters.

Unlike spin-flow filters that operate within bioreactors and are distinct from cross-flow filters in a few major aspects, hollow-fiber filters operate externally and outside of the bioreactor. When in use, the cell culture fluid from the bioreactor is pumped to the housing where the filter is located and is concentrated as it flows across a membrane. The concentrated suspension stream is recycled to the bioreactor, while the cell-free filtrate forms the effluent stream and flows to the next unit operation, e.g., protein A column, for further purification and separation of the protein products. Because of fouling, presently, the hollow-fiber filters must be replaced every 5-7 days, i.e., once or twice during a perfusion cell culture. Replacing filters involves cost, labor and the risk of introducing contamination or variation in cell culture conditions, which negatively affect the perfusion cell culture operation.

Therefore, fouling remains a problem for filter-based cell retention devices, particularly those with hollow-fiber filters. Fouling reduces efficiency and life time of the filters and does not allow filters to function consistently over a long period of time. Another problem is the lack of a stable and scalable technology for preventing fouling or sieving in filter-based cell retention devices. As Bonham-Carter et al. suggested, some technologies such as TFF have been abandoned because of their scalability limitations or lack of proven market acceptance.

Accordingly, a need exists for improved retention devices and filters that overcome the problems discussed above.

BRIEF SUMMARY

The subject technology is based in part on the surprising discovery that large pore size (~5-10 µm) hollow-fiber filters operating in a TFF mode solve the fouling problems in perfusion culture systems, and operate efficiently and consistently for up to 35 days without significantly losing their product sieving capabilities. The cell retention devices and methods of the subject technology achieve high product sieving by TFF without a need for special treatment (e.g., gas scrubbing), without a need for a special design to increase pressure gradient across the filter (including the application of back pressure or increasing shear or flow rate), without a need to change the perfusion rate, without a need maintaining a particular perfusion volume in relation to the volume of the cell retention device, or without a need for treating the cell culture fluid (bioreactor contents) with a particular composition (e.g., a composition containing oxygen) before circulating the cell culture fluid through the cell retention device of the subject technology.

The subject technology is illustrated, for example, according to various aspects described below.

In an aspect, the subject technology relates to a cell retention device containing a hollow-fiber filter having an average pore size ranging from about 0.5 to about 20 µm. In one or more embodiments, directly or indirectly, related to this aspect: the cell retention device is external to a perfusion cell culture vessel; the hollow-fiber filter has an average pore size selected from about 5 to about 8 µm, 5 µm to 15 µm, 5.2 µm to 12 µm, 5.5 µm to 8 µm, 5.2 µm to 7.7 µm, 5 µm, 6 µm, 7 µm, 8 µm, 9 µm, 10 µm, 11 µm, 12 µm, 13 µm, 15 µm, or any size above 5 µm that could retain the viable cells while allowing dead cells, cellular debris or macromolecules to pass through the filter; the hollow-fiber filter has an average pore size that is equal or greater than 5 µm but less than the size of viable cells being cultured in a cell culture vessel; the hollow-fiber filter has an average pore size greater than the size of a viable cell by 5 µm or less; the cell retention device is configured to operate by tangential-flow filtration (TFF) or by alternating tangential flow filtration (ATF); the TTF or ATF are configured to operate under a low shear rate of about 1000 s-1 to about 4000 s-1; the hollow-fiber filter has filter capacity of about 1000 to about 10,000 L/M2; the cell retention device is configured to operate in conjunction with a perfusion culture vessel; the hollow-fiber filter is made out of ceramic, polymer or metallic materials; the hollow-fiber filter operates for up to 35 days without being clogged or losing more than 10% of its product sieving ability; the hollow-fiber filter operates in TTF or ATF modes under a low shear rate of 2000 s-1 or less or a perfusion flow rate of equal or greater than 4000 L/M2; the hollow-fiber filter is in a housing that facilitates the collection of filtrates.

In another aspect, the subject technology relates to a method for harvesting recombinant protein products from a perfusion culture vessel, said method including the steps of: (a) subjecting cell culture fluid of a perfusion culture vessel to a cell retention device to be filtered, wherein the cell culture fluid comprises cells and recombinant protein products produced by said cells and wherein the cell retention device comprises a hollow-fiber filter having an average pore size ranging from about 0.5 to about 20 µm; (b) collecting filtrate from the cell retention device, wherein the filtrate comprises the recombinant protein products; and (c) Recirculating the filtered cell culture fluid to the perfusion culture vessel. In one or more embodiments, directly or indirectly, related to this aspect: the cell retention device is external to the perfusion cell culture vessel; the hollow-fiber filter filters the cell culture fluid by tangential-flow filtration (TFF) or alternating tangential flow filtration (ATF); the hollow-fiber filter has an average pore size selected from about 5 to about 8 micron, 5 µm to 15 µm, 5.2 µm to 12 µm, 5.5 µm to 8 µm, 5.2 µm to 7.7 µm, 5 µm, 6 µm, 7 µm, 8 µm, 9 µm, 10 µm, 11 µm, 12 µm, 13 µm, 15 µm, or any size above 5 µm that could retain the viable cells while allowing dead cells, cellular debris or macromolecules to pass through the filter; the hollow-fiber filter has an average pore size that is equal or greater than 5 micron but less than the size of the cells; the hollow-fiber filter has an average pore size greater than the size of the cells by 5 µm or less; the hollow-fiber filter has an average pore size that is about the size of the cells; the hollow-fiber filter is made out of ceramic, metallic or polymer materials; the filtrate comprises the recombinant protein products but lacks viable cells; the hollow-fiber filter operates for up to 35 days without being clogged or losing more than 10% of its product sieving ability; the cell retention device operates in TTF or ATF modes under a low shear rate of about 1000 s-1 to about 4000 s-1; the hollow-fiber filter has filter capacity of about 1000 to about 10,000 L/M2. In another embodiment, the subject technology relates to a protein made according to this aspect or to any of its embodiments.

In another aspect, the subject technology relates to a perfusion culture system, including: (a) a perfusion culture vessel configured to contain a cell culture fluid, wherein the cell culture fluid comprises liquid media, cells and recombinant protein products produced by said cells; (b) a cell retention device configured to receive the cell culture fluid and filter same to provide a filtrate comprising recombinant protein products, wherein the cell retention device comprises a hollow-fiber filter having an average pore size ranging from about 0.5 to about 20 µm; and (c) a pump and a fluid connector to circulate the cell culture fluid from the perfusion culture vessel to the cell retention device and back to the perfusion culture vessel. In one or more embodiments, directly or indirectly, related to this aspect: the cell retention device is external to the perfusion cell culture vessel; the cell retention device operates by tangential-flow filtration (TFF) or alternating tangential flow filtration (ATF); the hollow-fiber filter has an average pore size selected from about 5 to about 8 micron, 5 µm to 15 µm, 5.2 µm to 12 µm, 5.5 µm to 8 µm, 5.2 µm to 7.7 µm, 5 µm, 6 µm, 7 µm, 8 µm, 9 µm, 10 µm, 11 µm, 12 µm, 13 µm, 15 µm, or any size above 5 µm that could retain the viable cells while allowing dead cells, cellular debris or macromolecules to pass through the filter; the hollow-fiber filter has an average pore size that is equal or greater than 5 micron but smaller than the size of the cells; the hollow-fiber filter has an average pore size greater than the size of the cells by 5 µm or less; the hollow-fiber filter has an average pore size that is about the size of the cells; the filtrate comprises the recombinant protein products but lacks viable cells; the hollow-fiber filter is made out of ceramic, metallic or polymer materials or combination thereof; the hollow-fiber filter operates for up to about 35 days without being clogged or losing more than 10% of its product sieving ability; the cell retention device operates in TTF or ATF modes under a low shear rate of about 1000 s-1 to about 4000 s-1; the hollow-fiber filter has filter capacity of about 1000 to about 10,000 L/M2; the hollow-fiber filter allows the passage of macromolecules with a molecular weight of equal to or greater than 50 kD after 5 days of use without losing more than 10% of its product sieving ability;

the hollow-fiber filter allows the passage of macromolecules with a molecular weight of equal to or greater than 50 kD after 10 days of use without losing more than 10% of its product sieving ability; the filtrate is subjected to a Protein A column without a depth filtration step; the filtrate is subjected to a flocculation step before being subjected to a Protein A column; the cells comprise mammalian cells, plant cells, insect cells, yeast cells, or bacterial cells; the cells comprise BHK (baby Hamster kidney) cells, CHO (Chinese Hamster ovary) cells, HKB (hybrid of kidney and B cells) cells, HEK (human embryonic kidney) cells, and NS0 cells; the recombinant protein products are monoclonal antibodies or fragments thereof; the recombinant protein products are therapeutic proteins, hormones or enzymes.

BRIEF DESCRIPTION OF THE DRAWINGS

These and other features, aspects, and advantages of the claimed methods, apparatuses, and systems are better understood when the following detailed description is read with reference to the accompanying drawings:

FIG. 2 (right panel) is plot showing the filtration profiles of a 0.2 µm filter as a measure of sieving under two different flow conditions (TFF and ATF).

FIG. 3(A), left panel, shows that the % sieving is high for particles from the filtrate of another 0.2 µm membrane. FIG. 3(A), right panel, is the size distribution of the particles present in the filtrate. FIG. 3(B), left panel, shows that the % sieving continues to remain high for particles from CHO cell culture pellet resuspended in filtrate of another 0.2 µm membrane. FIG. 3(B), right panel, shows the size distribution of the particles from CHO cell culture pellet resuspended in filtrate of another 0.2 µm membrane. FIG. 3(C), left panel, shows that the % sieving is low for particles from cell culture supernatant of the bioreactor. FIG. 3(C), right panel, shows the size distribution of the particles from cell culture supernatant of the bioreactor.

DETAILED DESCRIPTION

Figure 1:
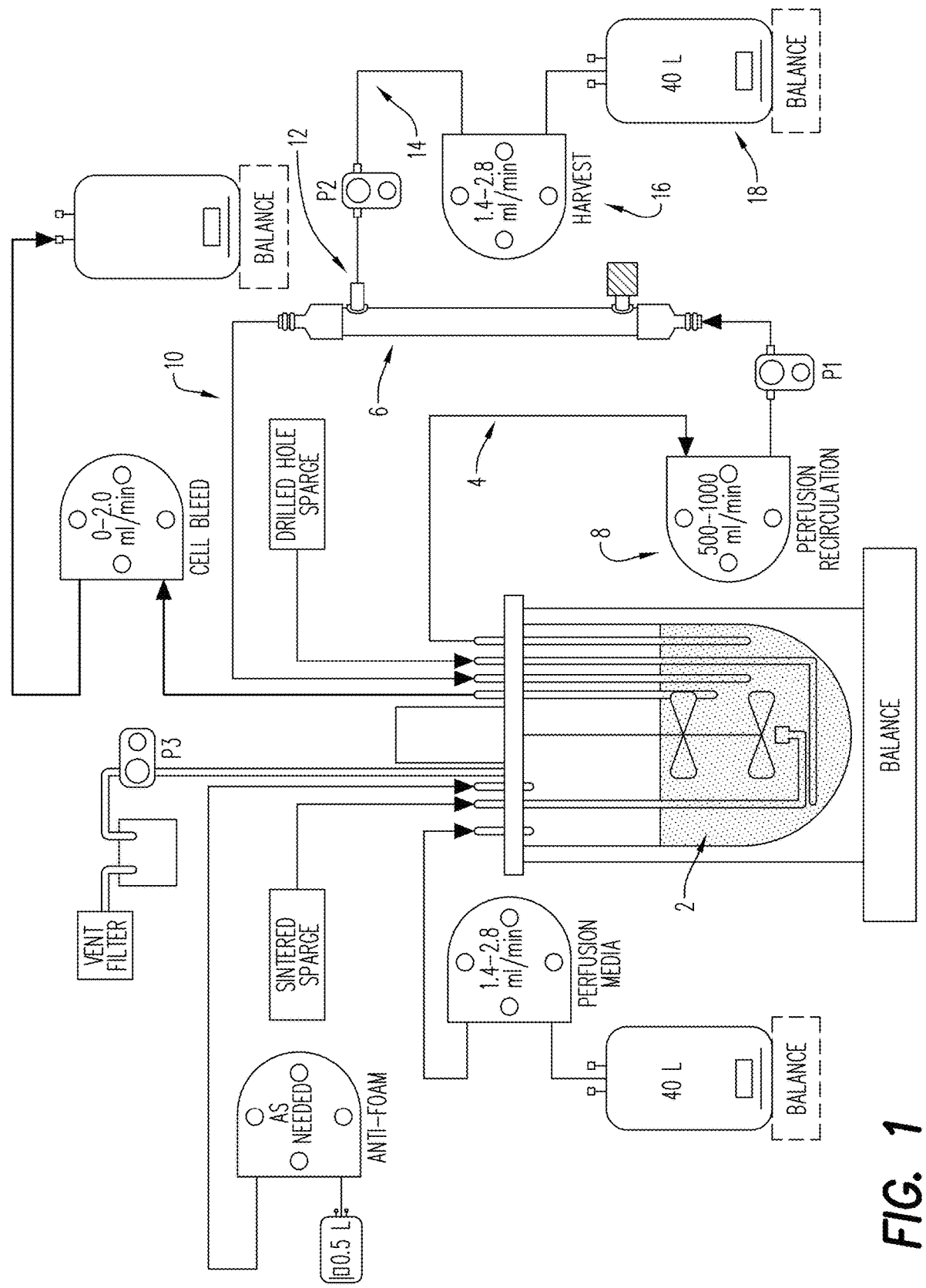
FIG. 1 is a schematic view of the cell retention device 6 of the subject technology shown in a typical perfusion cell culture system. A detailed explanation of the shown elements will be given below.

As provided above, the subject technology is based in part on the surprising discovery that that—in relation to the size of the product to be purified—comparatively large pore size (~5-10 µm average pore size) hollow-fiber filters operating in TFF or ATF modes solve the fouling problems in perfusion culture systems, operate efficiently and consistently for up to 35 days without significantly losing their product sieving capabilities.

Applicant have surprisingly discovered that the use of a larger pore size (~5-10 µm or ~5.2 to 7.7 µm average pore size) TFF membrane for perfusion CHO cell culture retention reduces or eliminates product loss due to molecular sieving inherent in membrane types commonly used today. This in turn enables a very long membrane lifespan (up to 35 days). The improvement in product yield may be up to 50% resulting in reduced cost to produce some biopharmaceuticals.

It is further surprising that the device and the method of the subject technology achieve their beneficial effects through a simplified operation, TFF, which others have abandoned. The operation of the device and method of the subject technology is simple because it involves no special treatment (e.g., gas scrubbing), no special design to increase pressure gradient across the filter (including the application of back pressure or increasing shear or flow rate), no need to change the perfusion rate, no need to maintain a particular perfusion volume in relation to the volume of the cell retention device, no need to treat the cell culture fluid (bioreactor contents) with a particular composition (e.g., a composition containing oxygen) before circulating the cell culture fluid through the cell retention device of the subject technology.

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Definitions:

To facilitate an understanding of the present subject technology, a number of terms and phrases are defined below:

The grammatical articles "one", "a", "an", and "the", as used herein, are intended to include "at least one" or "one or more", unless otherwise indicated. Thus, the articles are used herein to refer to one or more than one (i.e., to at least one) of the grammatical objects of the article. By way of example, "a component" means one or more components, and thus, possibly, more than one component is contemplated and may be employed or used in an implementation of the described embodiments.

The phrase "circulating or recirculating the cell culture fluid or the content of the bioreactor to and from the cell retention device" or an equivalent thereof as used herein means that the cell culture fluid (i.e., the content of the perfusion vessel) from a bioreactor is transferred from the bioreactor towards and into the retention device where the culture fluid is filtered in TTF or ATF modes and then is transferred or returned back to the bioreactor.

The term "retention device" as used herein is meant to include all devices with the ability to separate particles on basis of size or molecular weight. In particular, the cell retention device and method of the subject technology includes a hollow-fiber filter. The average pore size or molecular weight cut-off (MWCO) of the filter of the subject technology is chosen such that a desired separation between the viable cells and at least one of dead cells, cellular debris and/or macromolecules in the cell culture fluid can be established. Examples of filters suitable for use in the subject technology include membrane filters, ceramic filters and metal filters. The filter may be used in tubular or cylindrical shape. In an embodiment, the filter used in the cell retention device or method of the subject technology is a membrane filter, preferably a hollow-fiber filter.

The term "hollow-fiber filter" as used herein refers to a tubular or cylindrical-shaped membrane or filter which may be made out of aluminum oxide or other ceramic, stainless steel, or a multitude of polymers. A hollow-fiber filter has lumen with an internal diameter that could vary in size depending on the volume of the culture fluid that passes through it. The average pore size of the hollow-fiber filter is chosen such that the size of the pores is close to, or in some cases larger than, the size of the cells in the perfusion culture vessel. Suitable average pore size of the hollow-fiber of the subject technology is described below. In an example embodiment, the internal diameter of the hollow-fiber of the subject technology is between 0.2 and 10 mm. The length of the hollow-fiber of the subject technology is between 10 mm and 10 m. The surface area of the hollow-fiber of the subject technology is a multiple between 50 $cm^2$ and 25 $m^2$. The average pore size in the hollow-fiber of the subject technology ranges from about 0.5 μm to and up to the cell diameter or 20 μm.

The term "tangential flow" as used herein refers to a flow substantially parallel to the filter surface, for example, unidirectional tangential flow (TFF) or cross-flow.

The term "alternating tangential flow" as used herein refers to a flow arrangement in which a tangential flow travels back and forth along the membrane surface of a hollow-fiber filter and another flow travels in a direction substantially perpendicular to said filter surface. A tangential flow or an alternating tangential flow can be achieved according to methods known to the person skilled in the art.

For example, U.S. Pat. No. 6,544,424 describes methods for generating a alternating tangential flow in hollow fiber filters.

The term "product sieving" as used herein refers to measure of sieving which is the concentration of the product in the filtrate divided by the concentration of product in the culture vessel shown in percent. A product sieving of 100% suggests a good sieving conditions by which 100% of the product should pass through the filter. Over time, however, the amount of product passing through the filter decreases to below 100% due to fouling.

In one aspect, the subject technology relates to a fluid filtration system comprising a cell culture device including at least one filter containing housing, a fluid connector for directing the cell culture fluid from a cell culture vessel (bioreactor) to the cell culture device, at least one pump which powers the fluid in one or alternating direction(s) through the filter containing housing, and at least one fluid harvest port. The system is useful for conducting a rapid, low sheer, tangential flow filtration. Such a system has applications in perfusion cell culture systems or any other culture systems which requires retaining viable cells within the bioreactor.

Referring to FIG. 1 there is shown a fluid filtration system according to the subject technology within a typical perfusion bioreactor. A process vessel 2 is connected via a fluid connector 4 to a filter containing housing 6. The vessel 1 may be any suitable container for a fluid to be filtered. For example, it may be a bioreactor, a fermentor or any other vessel, nonexclusively including vats, barrels, tanks, bottles, flasks, containers, and the like which can contain liquids. The vessel may be composed of any suitable material such as plastic, metal such as stainless steel, glass, or the like. The fluid connector serves to direct a fluid from the process vessel into an entrance end of a filter containing housing 6.

A pump 8 is used to move the fluid from the vessel 2 through the fluid connector 4 into a hollow-fiber filter in the filter containing housing 6 and back to the vessel 2 through a fluid connector 10. In an embodiment, another pump may be located along the fluid connector 10 to operate in conjunction with the pump 8 to cause the fluid to move in reverse producing an alternating (back-and-forth) tangential flow through the filter containing housing 6 before the fluid is allowed to return back to the vessel 2. The entire filtration pathway shown in FIG. 1 is smooth with no crevices, sharp edges, constrictions, or turns, that would adversely affect cell vitality or viability.

The filter containing housing 6 also has at least one opening 12 which is suitable as a fluid harvest port. In an embodiment, a filtrate pump 16 is connected to the harvest line 14. The filtrate pump 16 is suitable as a means for controlling the removal of filtered fluid from the system and to serve as a check valve to regulate the unrestricted flow of filtrate from the filter containing housing 6. The filtrate pump 16 then moves the filtrate to a next unit operation which may be a storage tank 18 or a protein A column.

In short, FIG. 1 shows a system in which the cell culture fluid or the content of the perfusion vessel is pumped through the cell retention device of the subject technology in TTF or ATF modes to be filtered and then recirculated back to the perfusion vessel. The filtrate meanwhile is transferred to the next unit operation which may be a protein A column, a storage tank, a subsequent filtration unit, or a flocculation unit. In an embodiment, the filtrate in the storage tank 18 or an equivalent compartment may be subjected to flocculation (e.g., liquid extraction), e.g., mixed with a flocculent such as 100% PEG400 (707 kg/627 L) and/or 40% wt. phosphate (at 1553 kg/1128 L). As the result of the flocculation, the filtrate will separate into a 1:1 light and heavy phases. Depending on which phase the recombinant protein product is in (e.g., antibody products will stay in the light phase), that phase will be subjected to a protein A column chromatography for product purification.

In another aspect, the subject technology relates to a cell retention device with an average pore size ranging from 0.5 µm to 20 µm.

In another aspect, the subject technology relates to a method of harvesting cultured recombinant protein products from a perfusion culture vessel, said method including subjecting cell culture fluid from the culture vessel to a cell retention device to be filtered, collecting a harvest product output from the cell retention device, and recirculating the filtered cell culture fluid back to the culture vessel; wherein the harvest product output is the filtrate from the cell retention device and comprises the cultured recombinant protein product.

In another aspect, the subject technology relates to a perfusion cell culture system containing a perfusion culture vessel configured to contain cell culture fluid comprising liquid media and cells and recombinant protein products produced by said cells, a cell retention device configured to filter the cell culture fluid, and a pump and a fluid connector to circulate the cell culture fluid from the perfusion culture vessel to the cell retention device and back to the perfusion culture vessel.

In an embodiment relating to any of the above aspects of the subject technology, the cell retention device includes a hollow-fiber filter with an average pore size ranging from 0.5 µm to 20 µm or any fixed parameter or interval within this range, such as from 5 µm to 15 µm, or from 5.2 µm to 12 µm, or from 5.5 µm to 8 µm or from 5.2 µm to 7.7 µm. In a related embodiment, the average pore size of the hollow-fiber filter is, for example, 5 µm, or 6 µm, or 7 µm or 8 µm, or 9 µm, or 10 µm, or 11 µm, or 12 µm, or 13 µm, or 15 µm, or any size above 5 µm that could retain the viable cells while allowing dead cells, cellular debris or macromolecules to pass through the filter. In a related embodiment, the average pore size of the hollow-fiber filters of the subject technology has molecular weight cut-off (MWCO) value of about 50 kD, or about 100 kD, or about 500 kD, about 1000 kD. In another related embodiment, the average pore size of the hollow-fiber filter of the subject technology is close to the size of a viable cell (e.g., 15 to 20 µm). In another related embodiment, the average pore size of the hollow-fiber filter of the subject technology is larger than the size of a viable cell by about 5 µm, or by about 4 µm, or by about 3 µm, or by about 2 µm, or by about 1 µm, or by about 0.5 µm.

In another embodiment relating to any of the above aspects of the subject technology, the hollow-fiber filter of the subject technology has a surface area greater or equal to 10 cm$^2$. In a related embodiment, the surface area of the hollow-fiber filter of the subject technology is between 50 cm$^2$ and 50 m$^2$, or between 100 cm$^2$ and 25 m$^2$, or between 150 cm$^2$ and 20 m$^2$, or between 200 cm$^2$ and 15 m$^2$, or between 500 cm$^2$ and 10 m$^2$, or between 700 cm$^2$ and 70 m$^2$, or between 900 cm$^2$ and 90 m$^2$, or any fixed parameter or interval within said ranges.

In another embodiment relating to any of the above aspects of the subject technology, the hollow-fiber filter of the subject technology has an internal diameter (ID) that ranges from 0.2 mm to 20 cm or any fixed parameter or interval within this range, such as from 0.2 mm to 10 cm, or from 0.2 mm to 5 cm, or from 0.2 mm to 1 cm, or from 0.2 mm to 7 mm. In a related embodiment, the internal diameter is, for example, 0.2 mm, or 2 mm, or 4 mm, or 6 mm, or 8 mm, or 20 mm, or 200 mm.

In another embodiment relating to any of the above aspects of the subject technology, the hollow-fiber filter of the subject technology has a length of about 15 meter or less. In a related embodiment, the hollow-fiber filter of the subject technology has a length of about 25 cm, or about 50 cm, or about 1 m, or about 2 m, or about 3 m, or about 4 m, or about 5 m, or about 6 m, or about 7 m, or about 8 m, or about 9 m, or about 10 m, or about 11 m, or about 12 m, or about 13 m, or about 14 m, or about 15 m, In another embodiment relating to any of the above aspects of the subject technology, the hollow-fiber filter of the subject technology is made out of polymer, ceramic, metallic materials or a combination thereof. Examples of polymer resins from which the hollow-fiber filters of the subject technology may be made include, but is not limited to, modified or unmodified polyethersulfone (PES), modified or unmodified polyethylene (PE), a cellulose polymer, a modified or unmodified polyamide polymer, modified or unmodified polysulfone (PSF), modified or unmodified polyetherketone (PEK), modified or unmodified polyetheretherketone (PEEK), modified or unmodified polyvinylidene fluoride (PVDF), modified or unmodified polytetrafluoroethylene (PTFE), modified or unmodified polyvinylchloride (PVC), modified or unmodified polyvinylidene chloride (PVDC), or a mixture thereof. Examples of ceramic materials that may be used to produce the hollow-fiber filters of the subject technology include, but is not limited to, ceramic hydroxyapatite type I and II (CHT I, II), alpha-alumina, zirconia, titania, or any other ceramic material containing phosphorous, silica, calcium oxide, aluminum oxide, zinc oxide, titanium oxide and the like. Examples of ceramic filters that can be used according to the subject technology are Membralox® filters (from Pall Corporation) or equivalent filters. Examples of metallic materials that may be used to produce the hollow-fiber filters of the subject technology include, but is not limited to, stainless steel, low carbon steel, copper. Ceramic or metallic filters may be used as single or multiple use. Gamma sterilization, autoclave, or SIP (steam-in-place) are acceptable methods of sterilization before use. Cleaning may be carried out in CIP (Clean-In-Place) or COP (Clean Out of Place) modes.

In another embodiment relating to any of the above aspects of the subject technology, the hollow-fiber filter of the subject technology filters the cell culture fluid by tangential flow filtration (TFF). In a related embodiment, the hollow-fiber filter of the subject technology filters the cell culture fluid by alternating tangential flow filtration (ATF). In a related embodiment, the TFF cross flowrates is greater than zero but less than what could cause damage to the cells, for example high pressure or high shear conditions could cause cell lysis or have negative effect on cell culture conditions.

In another embodiment relating to any of the above aspects of the subject technology, the cell retention device of the subject technology operates under TTF or ATF conditions using low shear rates of about 1000 s$^{-1}$ to 4000 s$^{-1}$. In a related embodiment, the shear rates is about 1000 s$^{-1}$, or about 1500 s$^{-1}$, or about 2000 s$^{-1}$, or about 2500 s$^{-1}$, or about 3000 s$^{-1}$, or about 3500 s$^{-1}$, or about 4000 s$^{-1}$.

In another embodiment relating to any of the above aspects of the subject technology, the hollow-fiber filter of the subject technology as a filter capacity of about 500 L/m$^2$ to about 10,000 L/m$^2$. In a related embodiment, the hollow-fiber filter of the subject technology as a filter capacity of about 1000 L/m², or about 2000 L/m², or about 3000 L/m², or about 4000 L/m², or about 5000 L/m², or about 6000 L/m², or about 7000 L/m², or about 8000 L/m², or about 9000 L/m², or about 10,000 L/m².

In another embodiment relating to any of the above aspects of the subject technology, the hollow-fiber filter of the subject technology may be subjected to periodic backflushing by the filtrate/filtrate to reduce filter fouling.

In another embodiment relating to any of the above aspects of the subject technology, the cell retention device operates externally to or outside of a perfusion vessel. In another embodiment relating to any of the above aspects of the subject technology, the cell retention device houses the hollow-fiber filter of the subject technology. In a related embodiment, the filter housing that houses the hollow-fiber filter of the subject technology is made out of materials such as stainless steel, glass, PVDF or other plastic materials.

In another embodiment relating to any of the above aspects of the subject technology, the pump types used for circulating cell culture fluid through the cell retention device of the subject technology or for drawing filtrate from said cell retention device may be centrifugal, peristaltic, ATF, sinusoidal, rotary lobe, liquid ring, or piston or any other low shear equivalents. In a related embodiment, the filtrate flow is regulated using a positive displacement pump where the gauge pressure on the pump inlet is greater than zero. In another related embodiment, the recirculation pumping system should be of low-shear design in order to maintain high cell viability and to reduce the formation of suspended particles in solution.

In another embodiment relating to any of the above aspects of the subject technology, the hollow-fiber filter of the subject technology has a life span of up to 35 days before fouling could reduce its percent product sieving by more 10%, or by more than 20%, before it needs to be replaced or cleaned. In a related embodiment, the hollow-fiber filter of the subject technology has a life span of greater than 8 days and up to 35 days, or has a life span of greater than 10 days and up to 15 days, or has a life span of greater than 17 days and up to 35 days, or has a life span of greater than 21 days and up to 35 days, or has a life span of greater than 25 days and up to 35 days. In a related embodiment, the hollow-fiber filter of the subject technology has a life span of 10 to 35 days, or 12 to 35 days, or 15 to 35 days, or 17 to 35 days, or 20 to 35 days, or 25 to 35 days, or 27 to 35 days.

In another embodiment relating to any of the above aspects of the subject technology, the hollow-fiber filter of the subject technology allows the passage of macromolecules with a molecular weight of equal to or greater than 50 kD after 5 days of use without losing more than 10% of its product sieving ability. In a related embodiment, the hollow-fiber filter allows the passage of macromolecules with a molecular weight of equal to or greater than 50 kD after 10 days of use without losing more than 10% of its product sieving ability.

In another embodiment relating to any of the above aspects of the subject technology, known downstream practices can be employed to purify the recombinant protein produced. Typical purification processes can include cell separation, concentration, precipitation, chromatography, and filtration, or the like.

In another embodiment relating to any of the above aspects of the subject technology, where applicable, the filtrate from the cell retention device or the hollow-fiber filter is subjected to a Protein A column without a depth filtration step.

In another embodiment relating to any of the above aspects of the subject technology, where applicable, the filtrate from the cell retention device or the hollow-fiber filter is subjected to a flocculation or extraction step before being subjected to a Protein A column.

In another embodiment relating to any of the above aspects of the subject technology, the cell culture fluid includes liquid cell culture media, cells, and recombinant protein products. In general, he cell culture fluid may include amino acids, salts (such as potassium chloride, magnesium sulfate, sodium chloride, sodium phosphate, magnesium chloride, cupric sulfate, ferrous sulfate, zinc sulfate, ferric nitrate, selenium dioxide, calcium chloride and/or other salts that can be found in a cell culture fluid), vitamins (e.g., biotin, choline chloride, calcium pantothenate, folic acid, hypoxanthine, inositol, niacinamide, vitamin C, pyridoxine, riboflavin, thiamine, thymidine, vitamin B-12, pyridoxal, putrescine, and/or other vitamins that can be found in a cell culture fluid) or other components, such as dextrose, mannose, sodium pyruvate, phenol red, glutathione, linoleic acid, lipoic acid, ethanolamine, mercaptoethanol, ortho phosphorylethanolamine and/or other components that can be found in a tissue culture fluid.

In another embodiment relating to any of the above aspects of the subject technology, the cells used in the culture vessel of the subject technology, which produce the recombinant protein products, can be any eukaryotic or prokaryotic cells, including mammalian cells, plant cells, insect cells, yeast cells, and bacterial cells. In some embodiments, the cells are mammalian cells, such as, for example, BHK (baby Hamster kidney) cells, CHO (Chinese Hamster ovary) cells, HKB (hybrid of kidney and B cells) cells, HEK (human embryonic kidney) cells, and NSO cells. The mammalian cells can be recombinant cells expressing monoclonal antibodies.

In another embodiment relating to any of the above aspects of the subject technology, the recombinant protein products can be any protein product, including antibody molecules, monoclonal antibodies or fragments thereof, recombinant protein products such as coagulation factors, including for example factor VII, factor VIII, factor IX and factor X.

EXAMPLES

Example 1

Cell Retention Membranes and Culture Fluid Flow Profiles

Figure 2:
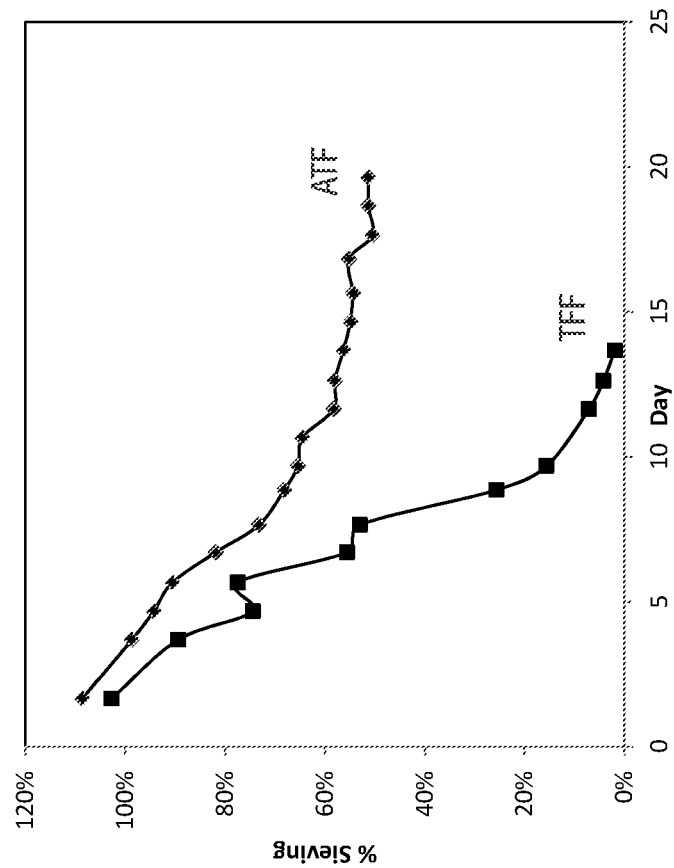
FIG. 2 (left panel) is a schematic view of a filter membrane (0.2 µm) in operation allowing cellular debris and products to pass as filtrates while retaining the viable cells (with a typical diameter of 12-15 µm).
Figure 2:
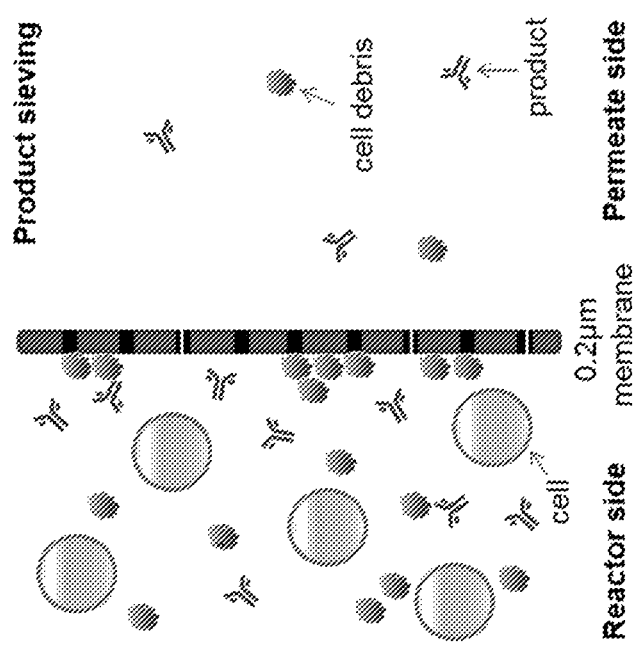

Cell retention membranes used for perfusion cell culture are often operated in tangential flow filtration mode (TFF) and are composed of polymer materials such as modified or unmodified Polystyrene (PS), Polyethersulfone (PES), Poly (vinylidene fluoride) (PVDF), etc. with pore sizes less than 0.2 micron. For many processes, it is desired that the cells are retained within the bioreactor, and that the spent media and product molecule pass through the filter material where it can be captured and purified. FIG. 2 (left panel). When in operation in a perfusion cell culture, and due to fouling (clogging) by cellular debris and macromolecules, filter membranes gradually lose their sieving capacity and behave as a molecular sieve inhibiting the transport of even the product molecules through the membrane, thereby dramatically reducing the product recovery. FIG. 2 (right panel). As shown in FIG. 2 (right panel), sieving capacity is measured in 0.2 micron filter membrane as a ratio of the product concentration in the filtrate to the product concentration in the bioreactor.

For good sieving conditions, 100% of the product should pass through the filter. Over time, however, the amount of product passing through the filter decreases. The sieving is better in the alternating tangential flow (ATF) filtration mode system than the TFF system. The ATF system is a pump system that appears to reduce the impact of the fouling. It is not a preferred system, and does not reduce the fouling completely, as shown on day 15, in which 50% of the product passes through the membrane. It is possible to pulse or backflow the filtrate as an attempt to reduce sieving, but this method has been met with limited success. Others have attempted to address the sieving problem mostly through changes in flow characteristics and to a lesser extent modifications to the filter membrane structure.

Example 2

Particle Size Distribution and Analysis

Figure 3:
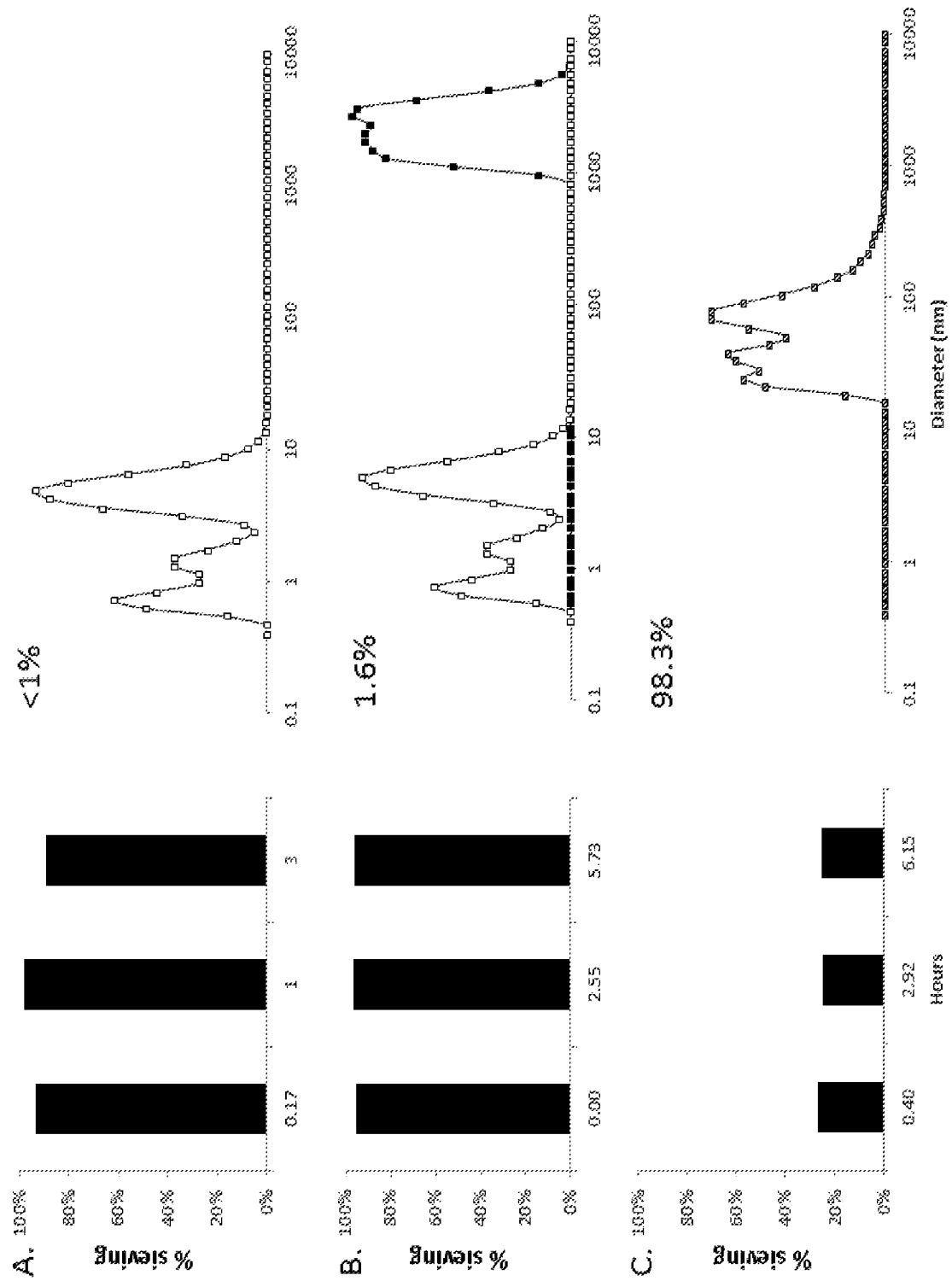
FIG. 3 shows the findings described in Example 2 with regard to the particle sizes of particles/debris present (A) in the filtrate of 0.2 µm filter, (B) in cell culture pellet resuspended in filtrate and (C) in cell culture supernatant.

The goal of this example was to determine the particle sizes of the particles/debris present in the filtrate of a 0.2 micron filter, cell culture pellet resuspended in filtrate, and cell culture supernatant. FIG. 3.

To determine which particle size range contributes the most to product sieving, cell culture was divided into three groups and assessed separately for product sieving offline using new 0.2 μm hollow fibers. To carry out this example, filtrate and cell culture were collected from a perfusion reactor on Day 8 of culture prior to the start of a cell bleed. The culture was centrifuged to separate cell culture material by size. Three distinct samples were thus obtained: A) the material in the filtrate stream (<10 nm in diameter), B) the cell pellet re-suspended in filtrate (<10 nm and >1 μm in diameter), and C) the material in the reactor supernatant.

Each separate section was then cycled through an unused 0.2 μm PS hollow fiber mimicking a perfusion setup. Samples from the filtrate and feed lines were taken at the indicated time points. Concentration of product was measured using the Cedex BioHT and product sieving expressed as concentration IgG in filtrate over concentration IgG in feed. Particle size analysis was conducted using a Malvern Zetasizer Nano ZS.

The particle size distributions as well as the subsequent poor sieving profiles are shown in FIG. 3. Samples (A) and (B) did not result in any significant product sieving for the entire duration of the experiment. FIG. 3 (A) and (B). When sample (C), cell culture supernatant containing primarily particles in the 100 nm size range, was introduced to a brand new 0.2 μm hollow fiber, product sieving was severe and almost instantaneous. FIG. 3 (C).

The results show that the materials/debris from the reactor supernatant, when passed through the TFF system, results in poor sieving at 0.4 hours and 6 hours of passage, while the larger and smaller particle sizes do not show poor sieving. It was concluded, then, that the particles/debris contained in the supernatant with sizes ranging from about 80 nm to 200 nm, or perhaps as much as 500 nm, cause the pore blockage in 0.2 μm filter leading to poor sieving.

Example 3

Filters with Pore Sizes Ranging from 0.45 μm to 500 KD

Based on the particle size distribution analysis conducted in Example 2, it was hypothesized that filter membranes with either larger or smaller pores than the debris should not block the pores.

Figure 4:
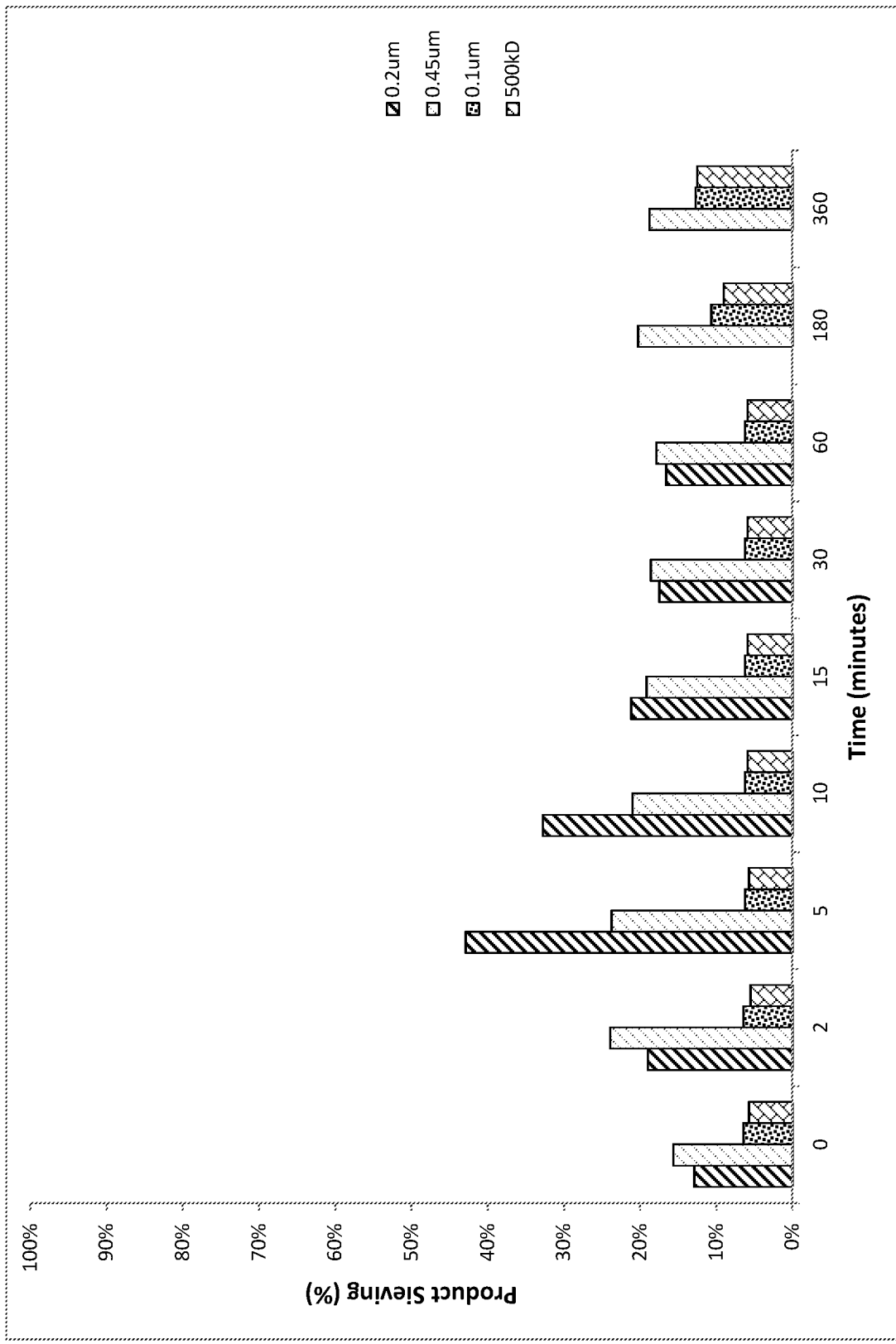
FIG. 4 is a schematic product sieving as a result of passing cell culture supernatant through hollow fibers with different pore sizes.

A range of pore sizes from 0.45 μm down to 500 kD were investigated. All demonstrated decreased product recovery throughout the entire time course of the experiment. The experimental results, however, showed that the smaller pore size membrane did not result in acceptable sieving profile. Moreover, the sieving profile was as poor as or even poorer than the 0.2 μm filter in membranes with larger pore sizes, e.g., 0.45 μm. FIG. 4.

It was concluded that pore sizes smaller than 0.2 μm did not help the product sieving phenomenon. Interestingly, utilizing a nominally larger pore size (0.45 μm) appeared to have no beneficial impact and even exacerbated product sieving at certain time points compared to the 0.2 μm.

Example 4

Filters with Larger Pore Sizes

In spite of the results of Example 3 relating to the filters with larger pore sizes than 0.2 μm and the teachings in the art regarding the lack of advantage of larger pore filters, Applicants set out to determine the sieving characteristics of hollow-fiber filters with even larger pore sizes (e.g., 5 to 7.7 μm). The hollow-fiber filter cartridges with pore sizes of 5 μm and above were obtained from Spectrum Laboratories, Inc. (Rancho Dominguez, CA).

It was expected that the larger pores would be blocked by the living cells, since the cells themselves were about the same size (~10 to 15 μm). Since membranes pore sizes have a wide range, a membrane with a nominal pore size of 5 μm may have pores between 1 μm to 15 μm. It was also expected that, due to the pore size distribution, cells would pass through the membrane or lyse in the membrane and foul the membrane quickly. The life time of the membrane was expected to be short (less than 100-500 L/m2). It was also anticipated that the larger pore size would cause the viable cells to lyse or become damaged because the pores are effectively rough on the length scale of the cell, and may puncture or damage the cells. It was also expected the smaller pores to foul quickly with smaller debris, and show sieving or low life time (less than or equal to 100-500 L/m2).

Figure 5:
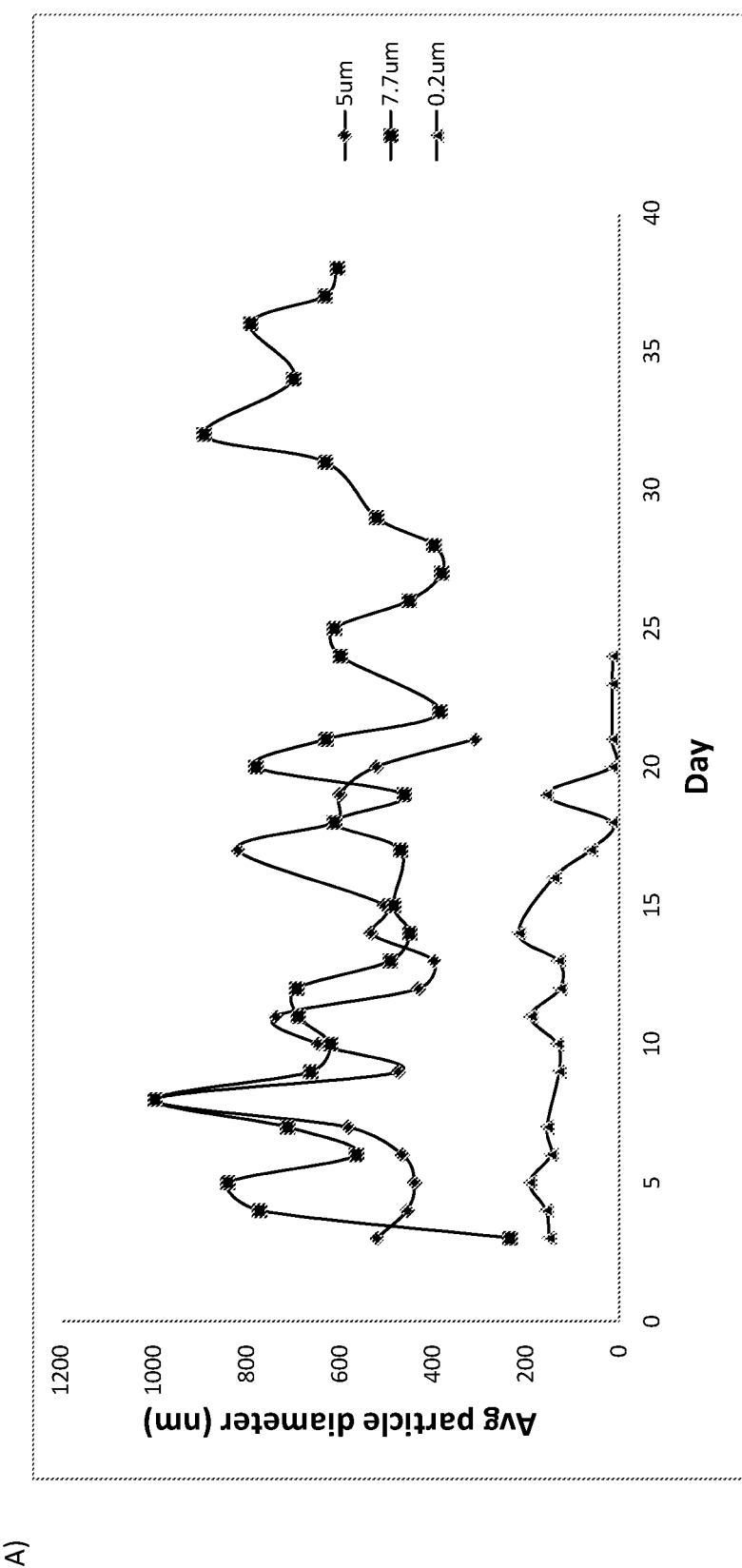
FIG. 5 shows the results of the particle size analysis of the filtrate using dynamic light scattering. Panel (A) shows a significantly larger primary peak, demonstrating that the material that passes through the 5 µm and 7.7 µm are composed of larger sized particles. Panel (B) shows the approximate number of particles in the cell culture supernatant (i.e., the materials that cannot make it across the membrane) that builds up as over time from perfusion cultures utilizing either a 0.2 µm, 5 µm or 7.7 µm pore size hollow fiber filters.
Figure 5:
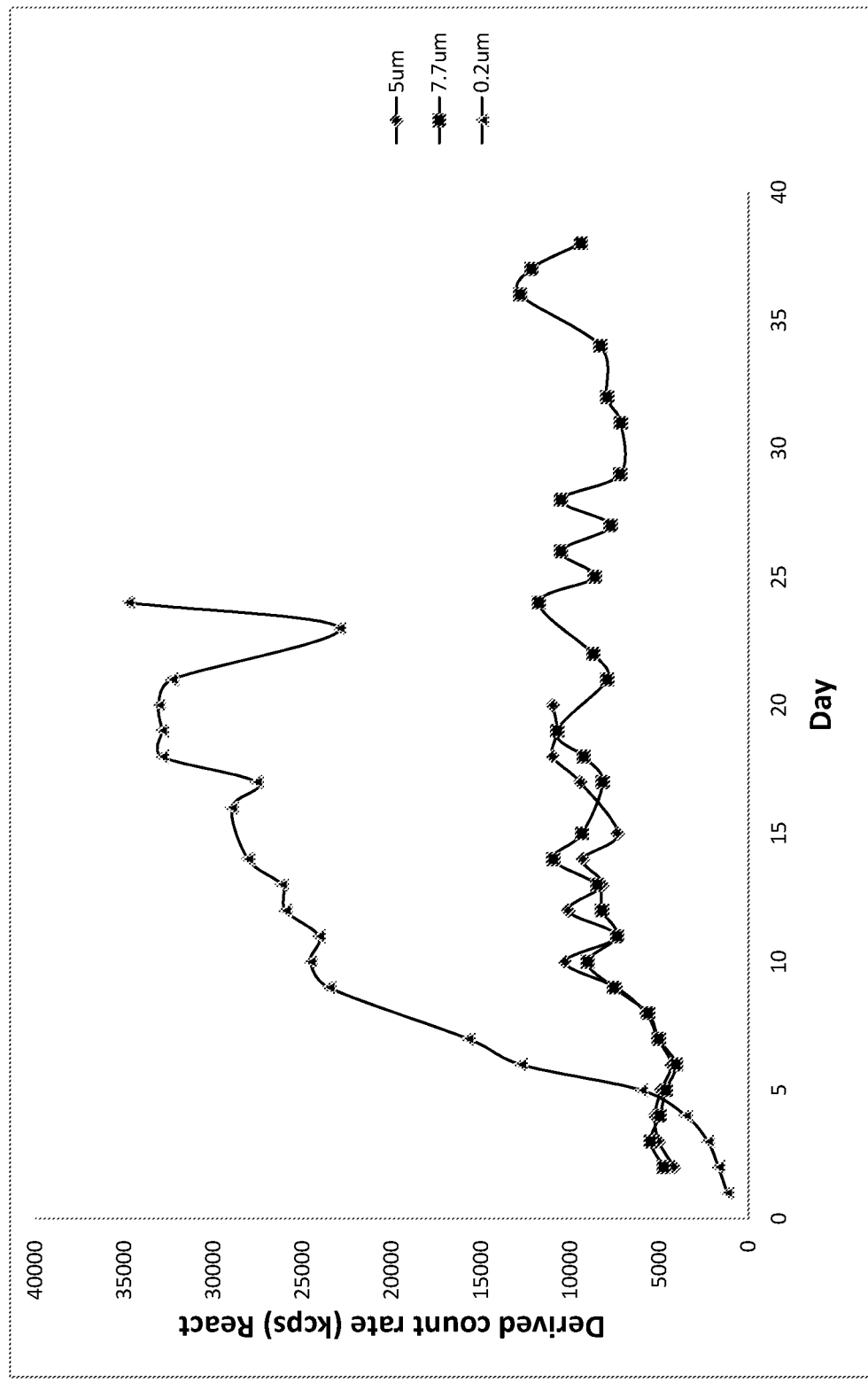

The results, however, was surprising. It was determined that going to even larger pore sizes (e.g., 5 to 7.7 μm) outside the normal range utilized in perfusion cell culture showed excellent sieving characteristics. FIG. 5. It was presumed that the cell debris pass through the filter, and, as shown in FIG. 5, it was determined that the particle size distribution of material in the filtrate is greater for the larger pore size filters.

Figure 6:
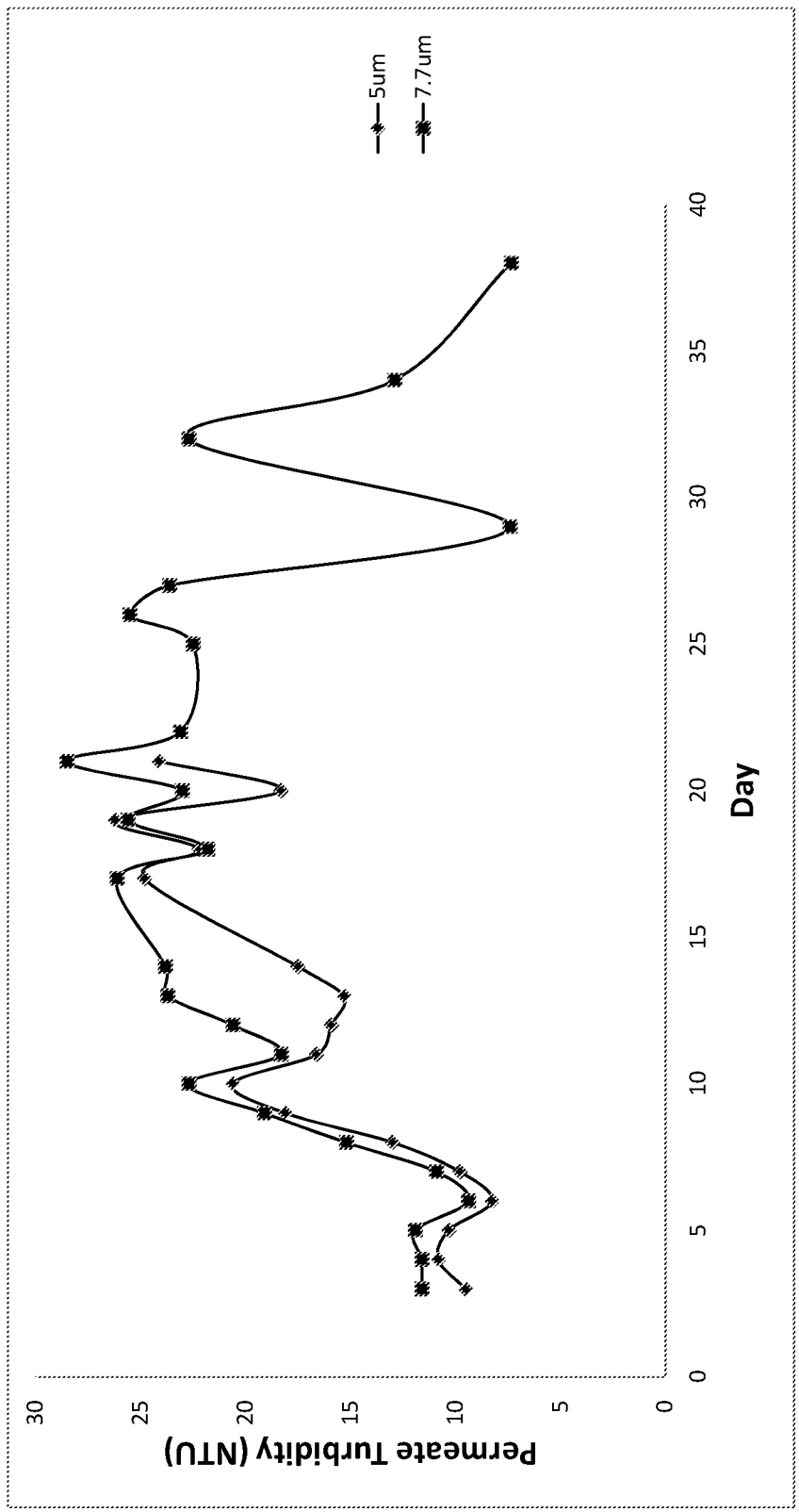
FIG. 6 is a plot showing the filtrate turbidity over time for hollow fiber filters with average pore sizes 5 and 7.7 µm used in a perfusion cells culture system.

Despite the greater amount of larger materials passing through the larger pore size membrane, however, the turbidity of the filtrate was surprisingly not too high. Surprisingly, the large pore size membrane was not blocked by the viable cells. Nor was the cell viability significantly negatively impacted. FIG. 6.

Example 5

Comparing 7 μm and 0.2 μm Filters in Perfusion Processes

In this example, percent product sieving of a hollow-fiber filter with an average pore size of 7 μm, according to the subject technology, was compared to that of a standard 0.2 μm hollow-fiber filter under similar perfusion cell culture conditions.

Figure 7:
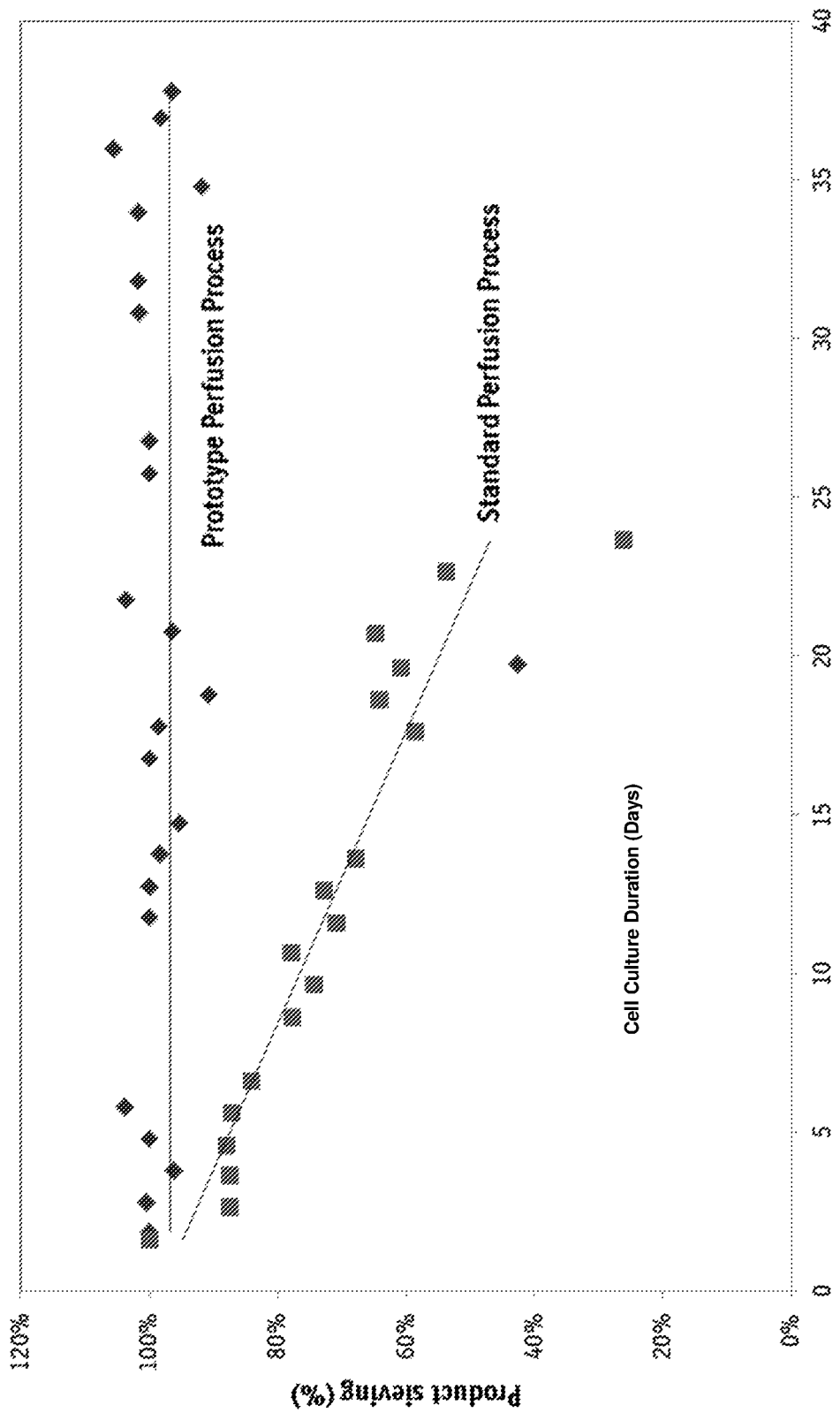
FIG. 7 shows the percent product sieving in a perfusion process in which the cell retention device contained a 7 µm pore-size hollow fiber filter (Prototype Perfusion Process according to the subject technology) as compared to a perfusion process in which the cell retention device contained a 0.2 µm pore-size hollow fiber filter (Standard Perfusion Process).

As shown in FIG. 7, the 7 μm pore-size allows excellent sieving characteristics throughout the duration of the perfusion process (i.e., prototype perfusion). In addition, surprisingly, the lifetime (or capacity) of the 7 µm membrane was quite high, in excess of 1000 L/m2, running upwards of 16,000 L/m2 for certain processes. This membrane life time was surprisingly high, especially given the dirty nature of the feed, which contained cells, debris, product, and spent media.

Example 6

The Effect of Filtrate on Protein A Column

As previously discussed, it was presume that the pore blocking cell debris pass through the filter, and, as shown in FIG. 5 above, it was seen that the particle size distribution of material in the filtrate is greater for the larger pore size. Surprisingly though, this extra debris load can be handled by the Protein A column without significant negative changes in behavior. One would expect a significant loss in the number of cycles a Protein A column could be run, but this was not observed as up to 42 cycles were performed without appearance of any abnormality. See Table 1.

TABLE 1

Protein A column load data with filtrate from a 7.71 µm hollow-fiber filter.
7.71 µm Filter - Protein A Load Data

| Cycle No. | Elution Vol (ml) | Eluate pool titer (g/L) | pH | mg eluted (mg) | mg loaded (mg) | Load Challenge (mg/mL of resin) | Load titer (mg/ml) | Yield (%) |
|---|---|---|---|---|---|---|---|---|
| 22 | 15 | 12.1 | 4.76 | 181.5 | 250.12 | 50.024 | 0.46 | 72.56 |
| 23 and 24 | 30 | 12.3 | 4.39 | 369 | 500.24 | 100.048 | 0.85 | 73.76 |
| 25 and 26 | 30 | 11.7 | 4.49 | 351 | 499.96 | 99.992 | 0.85 | 70.21 |
| 27 and 28 | 30 | 12.9 | 4.59 | 387 | 499.96 | 99.992 | 0.7 | 77.41 |
| 29 to 31 | 45 | 11.8 | 4.51 | 531 | 749.94 | 149.988 | 0.48 | 70.81 |
| 32 and 33 | 30 | 13.2 | 4.56 | 396 | 500.4 | 100.08 | 0.58 | 79.14 |
| 34 and 35 | 30 | 11.7 | 4.48 | 351 | 500.4 | 100.08 | 0.65 | 70.14 |
| 36 and 37 | 30 | 9.1 | 4.19 | 273 | 508.48 | 101.696 | 0.6 | 53.69 |
| 38 | 15 | 12.1 | 4.48 | 181.5 | 254.24 | 50.848 | 0.6 | 71.39 |
| 39 and 40 | 30 | 11.6 | 3.59 | 348 | 500 | 100 | 0.63 | 69.60 |
| 41 and 42 | 30 | 10.4 | 3.54 | 312 | 500.04 | 100.008 | 0.56 | 62.40 |

Surprisingly, other large molecular weight material secreted by the cells or as a result of cell lysis also pass through the 5 µm filter. This passage results in better and more consistent cell culture conditions. As an example, the enzyme LDH passes through the 5 µm filter but not as readily through the 0.2 µm filter (data not shown).

Figure 8:
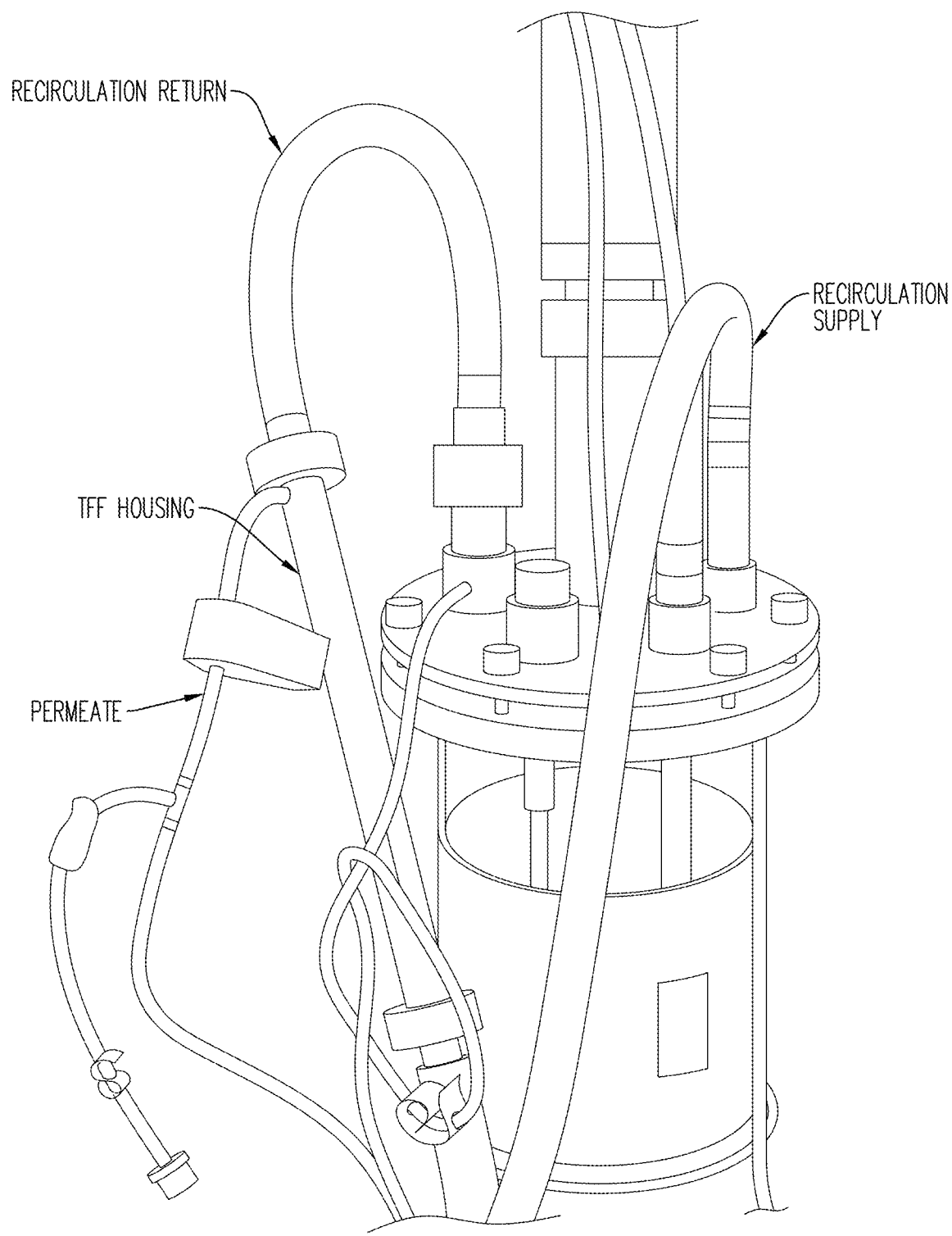
FIG. 8 is a photograph of a perfusion culture vessel connected to the cells retention device of the subject technology. The photograph shows a 5.0 micron ceramic TFF filter with stainless steel housing in operation. Also called a "straw" it has a lumen ID of 7 mm and length of 25 cm.

The larger pore size does allow the passage of impurities through the filter and into the downstream. While the impact of this debris does not significantly impact the Protein A column, methods of treating the filtrate to reduce the debris load can be conceived. Methods such as depth filtration, dead end filtration, TFF, accoustophoretic filtration, or the use of flocculants or low pH treatments can be used to reduce the debris load downstream. FIG. 8 provides a photograph of the cell retention device of the subject technology in operation.

Example 7

Filter Capacity

The aim of this experiment was to determine the filter capacity of a 5 µm hollow-fiber filter using two different cell lines.

Filter capacity is defined as volume of liquid perfused through the hollow fiber over the filter surface area. In this example, two different in-house proprietary recombinant Chinese Hamster Ovary (CHO) cell lines (Cell Lines 1 and 2) producing monoclonal antibodies were run in TFF perfusion mode in two separate perfusion bioreactors each equipped with a cell retention device containing a hollow-fiber filter with an average pore size of 5 µm, constructed of alpha alumina materials (Membralox microfiltration filters purchased from Pall, Deland, FL), with lumen diameter of 7 mm and surface area of 50 cm$^2$.

Figure 9:
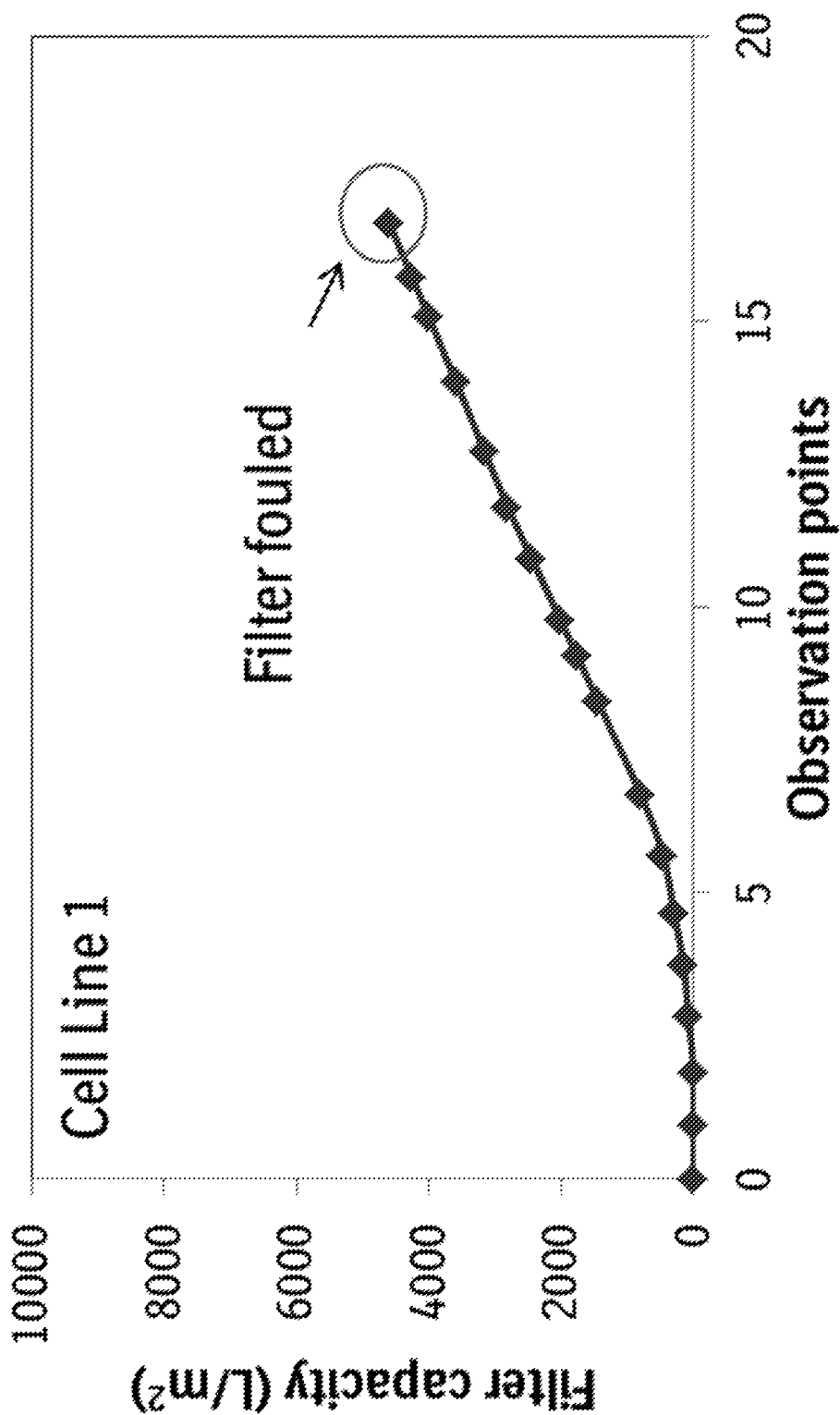
FIG. 9 displays two plots showing that the filter capacities are dependent on the cell lines being cultured in the bioreactor. Plot (A) shows that the filter used in the cell retention device has a filter capacity of greater than 4000 $L/m^2$ for proprietary recombinant Chinese Hamster Ovary (CHO) cell line 1. Plot (B) shows that the same filter as in (A) has a filter capacity of greater than 8000 $L/m^2$ for proprietary recombinant Chinese Hamster Ovary (CHO) cell line 2.
Figure 9:
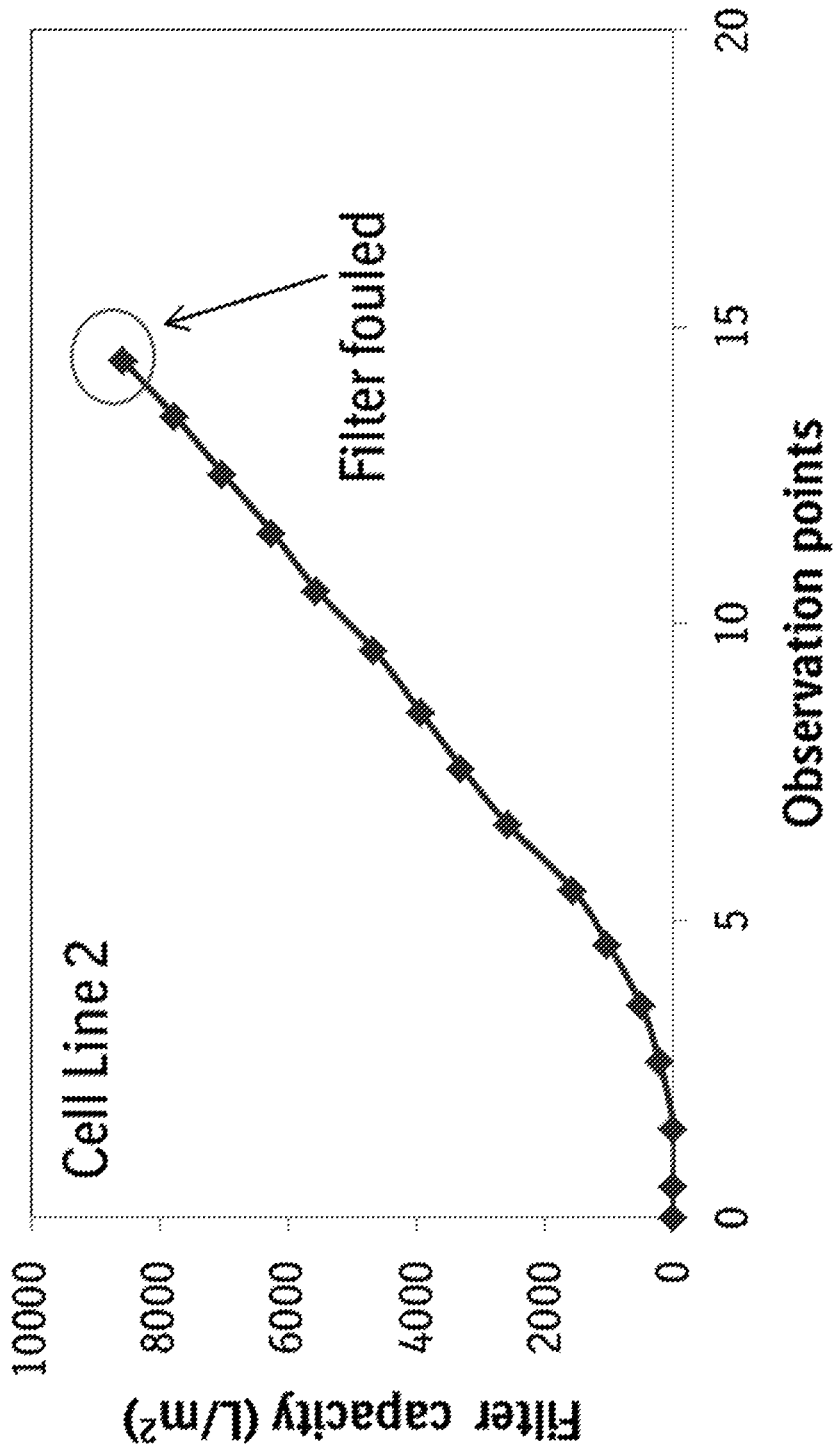

As shown in FIG. 9, panels (A) and (B), a nearly 2× difference in filter capacity is observed between the two cell lines. However, the filter capacity in both cases was surprisingly high (above 4000 L/m$^2$). The cell culture viability was maintained >90% in both bioreactors.

Therefore, it was determined that the filter capacity was dependent on the cell lines being retained. However, the results showed that the filter capacities of 5 µm hollow-fiber filters, used according to the subject technology, were surprisingly high (above 4000 L/m$^2$).

Example 8

Product Sieving Profile

The aim of this experiment was to determine the product sieving (recovery) profile of the hollow-fiber filters used in Example 7.

In this example, the in-house proprietary recombinant Chinese Hamster Ovary (CHO) cell lines 1 producing monoclonal antibodies were run in TFF perfusion mode in a perfusion bioreactor equipped with a cell retention device containing a hollow-fiber filter with an average pore size of 5 μm, constructed of alpha alumina materials (Membralox microfiltration filters purchased from Pall, Deland, FL), with lumen diameter of 7 mm and surface area of 50 cm$^2$ (as in Example 7).

Figure 10:
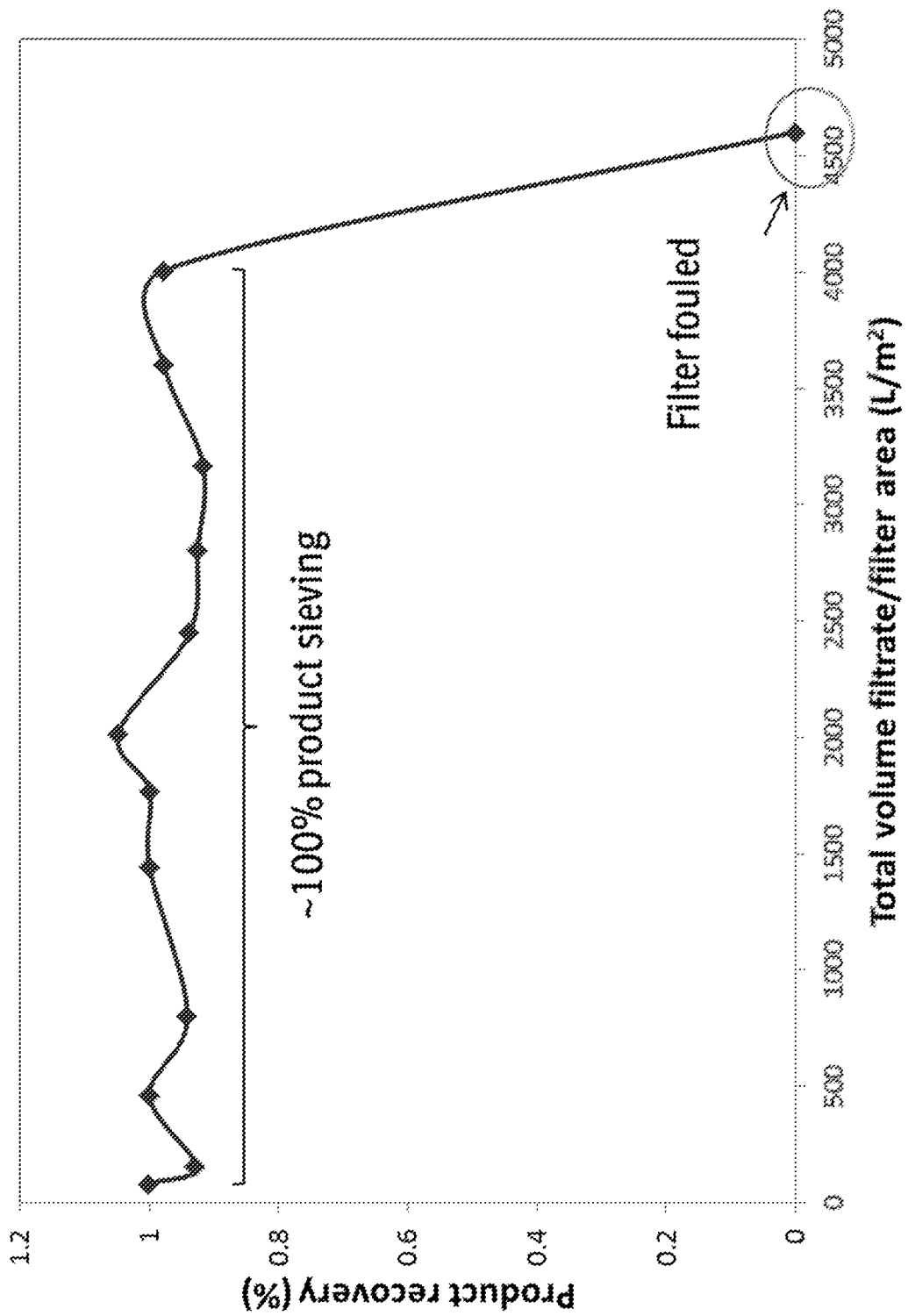
FIG. 10 is a plot showing the % product sieving of the hollow-fiber filter used in FIGS. 9(A) and (B). As shown, the % product sieving of the hollow-fiber filter of the subject technology remains continuously high until the filter capacity is reached.

As shown in FIG. 10, unlike the gradual decrease in product sieving of a 0.2 μm hollow-fiber, product sieving of the hollow-fiber filters, according to the subject technology, remains at nearly 100% up to and until the filter capacity is reached. This behavior or sieving profile was surprising and allows for nearly complete passage of product up until when membrane capacity is reached. In other words, the filters of the subject technology can be used for a long period of time with little or no decrease in product recovery up until the filter capacity is reached, which provides predictability and efficiency in recovering the maximum amount of products.

It will be apparent to those skilled in the art that various modifications and variations can be made to the described embodiments without departing from the spirit and scope of the claimed methods. Thus, it is intended that present claimed methods cover the modifications and variations of the embodiments described herein provided that they come within the scope of the appended claims and their equivalents.

INDUSTRIAL APPLICABILITY

The device and methods disclosed herein are useful for perfusion biomaufacturing, and thus for improving industrial methods for manufacturing recombinant, therapeutic proteins.

The invention claimed is:

1. A method for harvesting a recombinant monoclonal antibody from a perfusion culture vessel, said method comprising the steps of:
   a. culturing Chinese Hamster Ovary (CHO) cells expressing the recombinant monoclonal antibody in a perfusion culture in the perfusion culture vessel;
   b. subjecting the cell culture fluid of the perfusion culture vessel to a tangential flow filtration system comprising a hollow-fiber filter having an average pore size ranging from about 5 to about 8 microns, wherein the hollow-fiber filter has a filter capacity of 1,000 to 10,000 L/M$^2$,
   and wherein the hollow-fiber filter can retain at least 90% of its product sieving ability until the total volume of filtrate per m$^2$ of the hollow-fiber filter is greater than or equal to 1000 L/m$^2$ when the cell retention device is configured to run in tangential-flow filtration (TFF) perfusion mode;
   collecting the filtrate from the hollow fiber filter, wherein the filtrate comprises the recombinant monoclonal antibody; and
   d. recirculating the remaining cell culture fluid to the perfusion culture vessel.

2. The method of claim 1, wherein the cell retention device is external to the perfusion cell culture vessel.

3. The method of claim 1, wherein the hollow-fiber filter can retain at least 90% of its product sieving ability after 35 days when the cell retention device is configured to run in tangential-flow filtration (TFF) perfusion mode.

* * * * *